015# United States Patent [19]

Verheijen et al.

[11] 4,276,419
[45] Jun. 30, 1981

[54] PROCESS FOR THE PREPARATION OF C-SUBSTITUTED PYRIDINES AND/OR HYDROGENATED C-SUBSTITUTED PYRIDINES, C-SUBSTITUTED QUINOLINES AND/OR HYDROGENATED QUINOLINES

[75] Inventors: Egidius J. M. Verheijen, Born; Charles H. Geersheuvels, Geleen, both of Netherlands

[73] Assignee: Stamicarbon, B.V., Geleen, Netherlands

[21] Appl. No.: 78,587

[22] Filed: Sep. 19, 1979

[30] Foreign Application Priority Data

Sep. 20, 1978 [NL] Netherlands ................... 7809552

[51] Int. Cl.$^3$ ............... C07D 211/04; C07D 211/06; C07D 215/06; C07D 295/02
[52] U.S. Cl. ................................ 546/164; 546/195; 546/166; 546/249; 546/251; 546/185; 546/184; 546/181
[58] Field of Search ............ 546/166, 251, 249, 165, 546/164, 185, 184, 181

[56] References Cited

U.S. PATENT DOCUMENTS 3,007,931 11/1961 Simpson et al. ............... 546/251
3,247,209 4/1966 Schmerling ................... 546/166

FOREIGN PATENT DOCUMENTS 1304155 1/1973 United Kingdom .
1425698 2/1976 United Kingdom .

*Primary Examiner*—Alton D. Rollins
*Assistant Examiner*—D. B. Springer
*Attorney, Agent, or Firm*—Cushman, Darby & Cushman

[57] ABSTRACT

An improved process for the preparation of pyridines and/or hydrogenated pyridines that have been substituted with a hydrocarbon group at one or more carbon atoms, γ-cyanoketone, in a gaseous phase and in the presence of hydrogen, is passed in a reaction zone over a first catalyst containing a catalytically active metal or compound of a metal selected from the group copper, silver, gold, iron, nickel, cobalt, ruthenium, rhodium, palladium, osmium, iridium and platinum to form a reaction mixture. A hydrogen-containing gas is separated from the reaction mixture, passed over a second catalyst containing a catalytically active metal or compound of a metal selected from the group iron, nickel and cobalt at a temperature of between 300° and 800° C., and the hydrogen-containing gas so treated is recycled to the reaction zone.

5 Claims, No Drawings

PROCESS FOR THE PREPARATION OF C-SUBSTITUTED PYRIDINES AND/OR HYDROGENATED C-SUBSTITUTED PYRIDINES, C-SUBSTITUTED QUINOLINES AND/OR HYDROGENATED QUINOLINES

BACKGROUND OF THE INVENTION

The present invention relates to a process for the preparation of pyridines and/or hydrogenated pyridines that have been substituted with a hydrocarbon group at one or more of the carbon atoms. Such compounds are useful, for instance, in the preparation of pharmaceutical products and insecticides.

It is known that these compounds can be prepared by a γ-cyanoketone, in a gaseous phase and in the presence of hydrogen, over a catalyst containing a catalytically active metal or compound of a metal selected from the group consisting of copper, silver, gold, iron, nickel, cobalt, ruthenium, rhodium, palladium, osmium, iridium and platinum. A process of this type has been described in British Pat. Nos. 1,304,155 and 1,425,698. The gaseous reaction mixture obtained in this known process is predominantly hydrogen, usually containing from about 5 to 20% of other gases, and can be reused after being separated from the reaction mixture in the reaction of a further quantity of γ-cyanoketone.

It has been found, however, that when this hydrogen-containing gas is recycled, the selectivity and activity of the catalyst used in the reaction drops much more rapidly than it would without the recirculation of such hydrogen-containing gas.

It is therefore an objective of the present invention to provide an improved method for the preparation of substituted pyridines and/or hydrogenated pyridines wherein the hydrogen-containing gas separated from the resulting reaction mixture can be recycled without adverse effect on the selectivity and activity of the catalyst.

BRIEF DESCRIPTION OF THE INVENTION

This obejctive is achieved according to the present invention by passing the hydrogen-containing gas, after its separation from the reaction mixtures but prior to its recycle to the reaction zone, over a second catalyst containing a catalytically active metal or compound of a metal selected from the group consisting of iron, nickel and cobalt, at a temperature of between about 300° and 800° C. By so treating the hydrogen-containing mixture prior to recycle to the reaction zone, it has surprisingly been found that the relatively rapid deterioration of selectivity and activity of the reaction catalyst noted in the known recycle process can be substantially avoided.

In the improved process of this invention, commercially available catalysts containing nickel, iron and/or cobalt may be used for this treatment of the hydrogen-containing gas to be recycled. In these catalysts, the catalytically active component is usually supported on a carrier material such as, for example, alumina, silica, magnesia or carbon. A catalyst comprised of nickel on an alumina supporting carrier has been found particularly suitable for carrying out the present method.

The space velocity with which the hydrogen-containing gas to be recycled is passed over the catalyst may be varied within relatively wide limits, for example from between about 0.1 to 50 liters (N.T.P.) per gram of catalyst per hour. Preferably, however, a space velocity of between 0.25 and 20 liters (N.T.P.) of hydrogen per gram of catalyst per hour is used.

The temperature at which the hydrogen-containing gas to be recycled is passed over the catalyst may be varied within the range of from between about 300° to 800° C. However a temperature of between about 450° and 650° C. has been found very suitable. The pressure at which the hydrogen-containing gas to be recycled is treated is not critical and therefore atmospheric pressure is preferably used.

The improved method may be applied to the reaction of the same γ-cyanoketones as the known process, including, for example, 5-oxohexane nitrile, 5-oxoheptane nitrile, 4-methyl-5-oxohexane nitrile, 2-(β-cyanoethyl) cyclohexanone, 4-phenyl-5-oxohexane nitrile, and 4-methyl-5-oxoheptane nitrile. However the improved method of this invention is very suitable for the preparation of 2-methyl-pyridine, 2,3-lutidine and quinoline from the respective starting products 5-oxohexane nitrile, 4-methyl 5-oxohexane nitrile and 2-(β-cyanoethyl)-cyclohexanone.

When the improved process of this invention is carried out, it may be that the hydrogen originally introduced into the reaction zone is not completely pure, and impurities may be formed in the conversion of the cyanoketone. If this occurs, the concentration of impurities can be maintained at an acceptable level by venting part of the hydrogen to be separated from the reaction mixture.

DETAILED DESCRIPTION OF THE INVENTION

The present invention will be illustrated in greater detail by the following examples and comparative examples.

EXAMPLES I-V

A gaseous mixture of 5-oxohexane nitrile and hydrogen was obtained by evaporation of liquid 5-oxohexane nitrile and mixing the resulting vapor with hydrogen. This gaseous mixture was passed over a catalytic bed contained in a first tubular reactor 25 millimeters in diameter and 500 millimeters in length, and equipped with a heating jacket. The catalyst bed contained 50 grams of catalyst consisting of palladium on an alumina support, having 0.5% by weight palladium. The temperature of the catalyst bed was maintained at 240° C. The nitrile was passed over the catalyst bed at a space velocity of 0.15 gram per gram of catalyst per hour, and the space velocity of the hydrogen was 0.15 liter (N.T.P.) of hydrogen per gram of catalyst per hour.

The resulting reaction mixture was passed through an ice-cooled collecting vessel in which the reaction product condensed. The non-condensed gaseous reaction mixture which remained consisted mainly of hydrogen. This hydrogen-containing mixture was passed at elevated temperature (varied between 475° and 525° C.) through a second tubular reactor having a diameter of 10 millimeters and a length of 250 millimeters, and containing a bed of 2 grams of nickel catalyst consisting of 16.1% by weight Ni on a $SiO_2$ carrier (type Gl-22 of BASF). The hydrogen-containing gas so treated was then recycled to the inlet of the first reactor in which the 5-oxohexane nitrile was converted. The space velocity through the second reactor was varied between 0.75 and 7.5 liters (N.T.P.) of hydrogen per gram of nickel catalyst per hour. After an operating period of 100 hours the amount of 5-oxohexane nitrile introduced into the catalyst bed of the first reactor, and the amount of reaction product obtained, were measured for one hour under constant conditions. The amount of 5-oxohexane nitrile passed through was determined by measuring the loss in weight of liquid 5-oxohexane nitrile.

The collected reaction product was analyzed gas-chromatographically, and the results are compiled on the table below, together with the results of two comparative examples. In Comparative Example A, no hydrogen was recycled to the reactor, while in Comparative Example B, the hydrogen supplied to the reactor consisted of 90% recycled hydrogen, which, however, was recycled directly without any treatment in the second reactor. It can be seen from this table that using the improved method of the present invention gives the advantage of hydrogen recycle without sacrificing conversion of nitrile and selectivity toward 2-methyl pyridine in contrast to the known process using such recycle.

| Ex. | Catalyst Temp. °C. | Space Velocity Second Reactor | Conversion of Nitrile % | Selectivity 2-methyl Pyridine % | Selectivity 2-methyl Piperidine % |
| --- | --- | --- | --- | --- | --- |
| I | 550 | 3.75 | 100 | 84.0 | 4.7 |
| II | 475 | 3.75 | 99.8 | 83.8 | 4.5 |
| III | 600 | 3.75 | 100 | 84.1 | 4.6 |
| IV | 550 | 7.50 | 99.9 | 83.7 | 4.7 |
| V | 550 | 0.75 | 100 | 84.0 | 4.6 |
| A | — | — | 100 | 84.2 | 4.6 |
| B | — | — | 94.8 | 75.1 | 4.7 |

EXAMPLE VI

The experiment of Example I was repeated under similar conditions, but with the use of a different catalyst for the treatment of the hydrogen to be recycled. Specifically, a cobalt on kieselguhr catalyst having a cobalt content of 39% by weight (Co-0127 catalyst of Harshaw) was used. After an operating period of 100 hours, the conversion of the nitrile was 100%, the selectivity toward 2-methyl pyridine was 83.9% and the selectivity toward 2-methyl piperidine was 4.6%.

EXAMPLE VII

Example I and Comparative Examples A and B were repeated under the same conditions, but at 230° C., and starting with 4-methyl 5-oxohexane nitrile instead of 5-oxohexane nitrile.

In the repeated Example I, the conversion was 99.3%, the selectivity toward 2,3-dimethyl pyridine was 89.3% and the selectivity toward 2,3-dimethyl piperidine was 9.2%. In the repeat of Comparative Example A (without recirculation of hydrogen) these values were 99.6, 89.7 and 8.6%, respectively, and in the repeat of Comparative Example B (with recirculation of untreated hydrogen) and the values were 94.3, 79.3 and 9.3%, respectively.

EXAMPLE VIII

Example I and Comparative Examples A and B were repeated under the same conditions but at 230° C., and starting with 5-oxoheptane nitrile instead of 5-oxohexane nitrile.

In the repeat of Example I, the conversion was 99.2%, the selectivity toward 2-ethyl pyridine was 80.3%, and the selectivity toward 2-ethyl piperdine was 13.6%. In the repeat of Comparative Example A (without hydrogen recirculation) these values were 99.7, 80.4 and 13.3%, respectively, and in the repeat of Comparative Example B (with recirculation of untreated hydrogen) the values were 94.5, 74.5 and 14.2%, respectively.

EXAMPLE IX

2-$\beta$-cyanoethyl cyclohexanone was passed over 50 grams of the Pd catalyst in the way described in Example I. The temperature of the catalyst was maintained at 210° C. The space velocity of the cyanoketone was 0.15 gram per gram of catalyst per hour, and the space velocity of the hydrogen was 0.3 liter (N.T.P.) per gram of catalyst per hour. The hydrogen to be recycled was passed over the nickel catalyst at a temperature of 550° C. with the same space velocity as in Example I. For comparison, this experiment was repeated under similar conditions, except first without recirculation of hydrogen and again, except with recirculation of untreated hydrogen.

Comparing this example having recirculation of treated hydrogen to the comparative experiments, first without hydrogen recirculation and then with recirculation of untreated hydrogen, the conversion was 100, 100 and 96.4%, respectively, the selectivity toward quinoline was 1% in all three cases, the selectivity toward decahydroquinoline was 48, 48 and 44%, respectively, the selectivity toward 1,2,3,4-tetrahydroquinoline was 6, 6 and 7%, respectively, and the selectivity toward 5,6,7,8-tetrahydroquinoline was 41, 42 and 39%, respectively.

What is claimed is:

1. In a process for the preparation of pyridines and/or hydrogenated pyridines that have been substituted with a hydrocarbon group at one or more carbon atoms, by the steps of:

passing a $\gamma$-cyanoketone, in a gaseous phase in the presence of hydrogen, over a first catalyst in a reaction zone containing a catalytically active component selected from the group consisting of copper, silver, gold, iron, nickel, cobalt, ruthenium, rhodium, palladium, osmium, iridium, platinum and compounds thereof, thereby forming a reaction mixture containing said substituted pyridines and/or hydrogenated pyridines and hydrogen;

separating a hydrogen-containing gas from said reaction mixture; and recycling at least a portion of said hydrogen-containing gas to said reaction zone, the improvement wherein said hydrogen-containing gas, prior to being recycled to said reaction zone, is passed over a second catalyst containing a catalytically active component selected from the group consisting of iron, nickel, cobalt and compounds thereof at a temperature of between about 300° and 800° C.

2. The process of claim 1 wherein said hydrogen containing gas is passed over said second catalyst at a space velocity of between 0.25 and 20 liters (N.T.P.) per gram of catalyst per hour.

3. The process of claim 1 or 2 wherein said second catalyst is nickel on an alumina support.

4. The process of claim 1 or 2 wherein said hydrogen containing gas to be recycled is passed over said second catalyst at a temperature of between about 450° and 650° C.

5. The process of claim 1 wherein said $\gamma$-cyanoketone is selected from the group consisting of 5-oxohexane nitrile, 5-oxoheptane nitrile, 4-methyl-5-oxohexane nitrile, 2-($\beta$-cyanoethyl) cyclohexanone, 4-phenyl-5-oxohexane nitrile, and 4-methyl-5-oxoheptane nitrile.

* * * * *